United States Patent
Lee et al.

(10) Patent No.: US 9,655,584 B2
(45) Date of Patent: May 23, 2017

(54) COMPUTED TOMOGRAPHY APPARATUS AND METHOD OF CONTROLLING X-RAY BY USING THE SAME

(71) Applicant: SAMSUNG ELECTRONICS CO., LTD., Suwon-si (KR)

(72) Inventors: Jung-heon Lee, Hwaseong-si (KR); Do-il Kim, Suwon-si (KR); Min-kook Cho, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 44 days.

(21) Appl. No.: 14/485,037

(22) Filed: Sep. 12, 2014

(65) Prior Publication Data

US 2015/0078508 A1 Mar. 19, 2015

(30) Foreign Application Priority Data

Sep. 13, 2013 (KR) ........................ 10-2013-0110629

(51) Int. Cl.
*A61B 6/03* (2006.01)
*A61B 6/00* (2006.01)
(Continued)

(52) U.S. Cl.
CPC .............. *A61B 6/542* (2013.01); *A61B 6/032* (2013.01); *A61B 6/06* (2013.01); *A61B 6/08* (2013.01);
(Continued)

(58) Field of Classification Search
CPC ......... A61B 6/032; A61B 6/06; A61B 6/4021; A61B 6/405; A61B 6/469; A61B 6/488; A61B 6/542; A61B 6/544
(Continued)

(56) References Cited

U.S. PATENT DOCUMENTS

| 5,379,333 A | * | 1/1995 | Toth | A61B 6/032 378/108 |
| 5,400,378 A | * | 3/1995 | Toth | A61B 6/032 378/108 |

(Continued)

FOREIGN PATENT DOCUMENTS

| EP | 2564787 A1 | 3/2013 |
| JP | 11-235334 A | 8/1999 |

(Continued)

OTHER PUBLICATIONS

Communication dated Mar. 24, 2015, issued by the European Patent Office in counterpart European Application No. 14184640.2.

(Continued)

*Primary Examiner* — Allen C. Ho
(74) *Attorney, Agent, or Firm* — Sughrue Mion, PLLC

(57) ABSTRACT

A method of controlling an X-ray in a computed tomography (CT) apparatus includes: acquiring scout images of an object; setting an imaging region of the object in the acquired scout images; determining an outline of transverse axes lengths of the imaging region based on the transverse axes lengths of the imaging region; controlling X-rays emitted toward the object by adjusting a distance between elements of a transverse collimator of the CT apparatus according to the determined outline; and reconstructing a cross-sectional X-ray image of the object based on X-ray projection data generated by detecting the controlled X-rays.

22 Claims, 10 Drawing Sheets

(51) Int. Cl.
*A61B 6/06* (2006.01)
*A61B 6/08* (2006.01)
(52) U.S. Cl.
CPC ............ *A61B 6/405* (2013.01); *A61B 6/4021* (2013.01); *A61B 6/469* (2013.01); *A61B 6/488* (2013.01); *A61B 6/544* (2013.01); *A61B 6/586* (2013.01)
(58) Field of Classification Search
USPC .......................................... 378/16, 108–110
See application file for complete search history.

(56) References Cited

U.S. PATENT DOCUMENTS

| | | | | |
|---|---|---|---|---|
| 5,450,462 | A * | 9/1995 | Toth ....................... | A61B 6/032 378/108 |
| 5,822,393 | A * | 10/1998 | Popescu ................. | A61B 6/032 378/108 |
| 5,867,555 | A * | 2/1999 | Popescu ................. | A61B 6/032 378/16 |
| 6,335,979 | B1 | 1/2002 | Seto et al. | |
| 6,385,280 | B1 * | 5/2002 | Bittl ....................... | A61B 6/032 378/106 |
| 6,445,761 | B1 * | 9/2002 | Miyazaki ............... | A61B 6/032 378/16 |
| 6,453,008 | B1 * | 9/2002 | Sakaguchi .............. | H04N 5/32 250/370.09 |
| 6,490,337 | B1 * | 12/2002 | Nagaoka ................ | A61B 6/032 378/16 |
| 6,754,301 | B2 * | 6/2004 | Horiuchi ................ | A61B 6/032 378/16 |
| 6,904,127 | B2 * | 6/2005 | Toth ....................... | A61B 6/032 378/108 |
| 6,907,100 | B2 * | 6/2005 | Taguchi ................. | A61B 6/032 378/19 |
| 6,987,828 | B2 * | 1/2006 | Horiuchi ............... | G01N 23/046 378/108 |
| 7,042,977 | B2 * | 5/2006 | Dafni ..................... | A61B 6/032 378/16 |
| 7,082,183 | B2 * | 7/2006 | Toth ....................... | A61B 6/032 378/16 |
| 7,103,139 | B2 * | 9/2006 | Nagaoka ................ | A61B 6/032 378/16 |
| 7,113,569 | B2 * | 9/2006 | Okumura ............... | A61B 6/032 378/150 |
| 7,142,630 | B2 * | 11/2006 | Suzuki ................... | A61B 6/542 378/108 |
| 7,215,733 | B2 * | 5/2007 | Nabatame .............. | A61B 6/032 378/110 |
| 7,245,691 | B2 * | 7/2007 | Kiyono .................. | A61B 6/032 378/4 |
| 7,336,762 | B2 * | 2/2008 | Seto ....................... | A61B 6/032 378/110 |
| 7,599,472 | B2 * | 10/2009 | Bernhardt .............. | A61B 6/08 378/137 |
| 7,602,880 | B2 * | 10/2009 | Hirokawa .............. | A61B 6/032 378/108 |
| 7,639,776 | B2 * | 12/2009 | Gohno ................... | A61B 6/032 378/109 |
| 7,668,286 | B2 * | 2/2010 | Tsuyuki ................. | A61B 6/032 378/16 |
| 7,688,938 | B2 * | 3/2010 | Paliwal .................. | A61B 6/032 378/16 |
| 7,711,085 | B2 * | 5/2010 | Suzuki ................... | A61B 6/14 378/39 |
| 7,756,242 | B2 * | 7/2010 | Kudo ..................... | A61B 6/032 378/15 |
| 7,778,381 | B2 * | 8/2010 | Nishide ................. | A61B 6/032 378/109 |
| 7,912,175 | B2 * | 3/2011 | Iisaku .................... | A61B 6/032 378/51 |
| 7,945,013 | B2 * | 5/2011 | Goto ...................... | A61B 5/4869 378/16 |
| 7,983,457 | B2 * | 7/2011 | Toth ....................... | A61B 6/032 378/16 |
| 8,031,831 | B2 * | 10/2011 | Zou ........................ | A61B 6/032 378/108 |
| 8,175,217 | B2 * | 5/2012 | Sugaya .................. | A61B 6/032 378/16 |
| 8,218,721 | B2 * | 7/2012 | Raupach ................ | A61B 6/032 378/150 |
| 8,396,184 | B2 * | 3/2013 | Shinno .................. | A61B 6/032 378/5 |
| 8,649,479 | B2 * | 2/2014 | De Man ................ | A61B 6/032 378/16 |
| 8,649,480 | B2 * | 2/2014 | Yoshida ................ | A61B 6/032 378/16 |
| 8,744,039 | B2 * | 6/2014 | Hirokawa .............. | A61B 6/032 378/16 |
| 8,848,860 | B2 * | 9/2014 | Yazaki ................... | A61B 6/488 378/16 |
| 8,942,341 | B2 * | 1/2015 | Hsieh ..................... | A61B 6/032 378/158 |
| 9,008,269 | B2 * | 4/2015 | Wang ..................... | A61B 6/52 378/146 |
| 9,177,682 | B2 * | 11/2015 | Proksa ................... | A61B 6/032 |
| 9,295,434 | B2 * | 3/2016 | Herold ................... | A61B 6/032 |
| 2004/0202283 | A1 | 10/2004 | Okumura et al. | |
| 2008/0080664 | A1 | 4/2008 | Bernhardt et al. | |
| 2009/0041191 | A1 | 2/2009 | Suzuki et al. | |
| 2012/0128120 | A1 | 5/2012 | De Man et al. | |
| 2013/0077738 | A1 | 3/2013 | Kreisler et al. | |

FOREIGN PATENT DOCUMENTS

| | | |
|---|---|---|
| JP | 2004208799 A | 7/2004 |
| JP | 200614822 A | 1/2006 |
| JP | 2006-314774 A | 11/2006 |
| KR | 1020070082138 A | 8/2007 |
| WO | 2012042484 A1 | 4/2012 |

OTHER PUBLICATIONS

Communication dated Mar. 31, 2015, issued by the Korean Intellectual Property Office in counterpart Korean Application No. 10-2013-0110629.

Communication dated Nov. 21, 2014 issued by the Korean Intellectual Property Office in counterpart Korean Patent Application No. 10-2013-0110629.

* cited by examiner

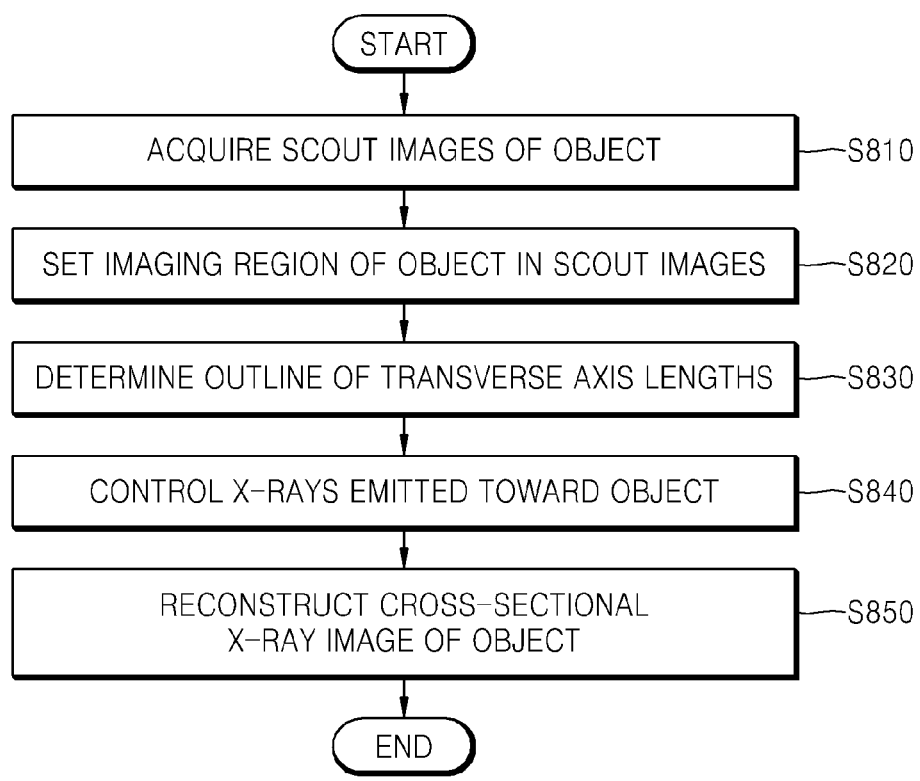

COMPUTED TOMOGRAPHY APPARATUS AND METHOD OF CONTROLLING X-RAY BY USING THE SAME

CROSS-REFERENCE TO RELATED APPLICATION

This application claims priority from Korean Patent Application No. 10-2013-0110629, filed on Sep. 13, 2013, in the Korean Intellectual Property Office, the disclosure of which is incorporated herein in its entirety by reference.

BACKGROUND

1. Field

One or more exemplary embodiments relate to a medical imaging apparatus, and more particularly, to a computed tomography (CT) apparatus and a method of controlling X-rays in the CT apparatus.

2. Description of the Related Art

A medical imaging apparatus acquires an image of an internal structure of an object through non-invasive inspection to visualize details of internal body structures, internal organs, and fluid flow. Examples of the medical imaging apparatus include a magnetic resonance imaging (MRI) apparatus, a CT apparatus, an X-ray apparatus, and an ultrasound apparatus.

The CT apparatus may provide a cross-sectional image of an object and achieve a non-overlapping representation of an internal structure (e.g., organs such as the kidneys and the lungs), as compared to a general X-ray apparatus.

The CT apparatus acquires X-ray images by transmitting X-rays to an object. However, during a CT scan, the object may be exposed to a high dose of uncontrolled X-rays, and the lifetime of a detector for detecting X-rays may be reduced. Thus, there is a need for a method of effectively controlling X-rays emitted by a CT apparatus.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include a computed tomography (CT) apparatus and a method of controlling an X-ray by using the same, which are adapted to control a transverse axis length.

One or more exemplary embodiments include a CT apparatus and a method of controlling an X-ray by using the same, which are adapted to increase the life span of a detector and reduce the amount of X-rays that are emitted toward an object.

According to one or more exemplary embodiments, a method of controlling an X-ray in a CT apparatus includes: acquiring scout images of an object by using images of the object that are respectively taken at a plurality of points along a rotation path of a rotating frame of the CT apparatus; setting an imaging region of the object in the acquired scout images; determining an outline of transverse axis lengths of the imaging region along the rotation path of the rotating frame based on transverse axis lengths of the imaging region; controlling X-rays emitted toward the object by adjusting a distance between elements of a transverse collimator in the CT apparatus according to the determined outline; and reconstructing a cross-sectional X-ray image of the object based on X-ray projection data generated by detecting the controlled X-rays.

According to one or more exemplary embodiments, a CT apparatus includes: a rotating frame including an X-ray emitter for emitting X-rays toward an object and a detector for detecting the X-rays emitted from the X-ray emitter and generating projection data; a scout image obtainer for acquiring scout images of the object by using images of the object that are taken at a plurality of points along a rotation path of the rotating frame; an imaging region setter for setting an imaging region of the object in the acquired scout images; a central controller for determining an outline of transverse axis lengths of the imaging region along the rotation path of the rotating frame based on transverse axis lengths of the imaging region; an X-ray controller for controlling X-rays emitted toward the object by adjusting a distance between elements of a transverse collimator according to the determined outline; and an image reconstructor for reconstructing a cross-sectional X-ray image of the object based on X-ray projection data generated by detecting the controlled X-rays.

BRIEF DESCRIPTION OF THE DRAWINGS

The above and/or other aspects will become more apparent by describing certain exemplary embodiments, with reference to the accompanying drawings, in which:

FIG. 8 is a flowchart of a method of controlling an X-ray in the CT apparatus, according to an exemplary embodiment;

DETAILED DESCRIPTION

Figure 1B:
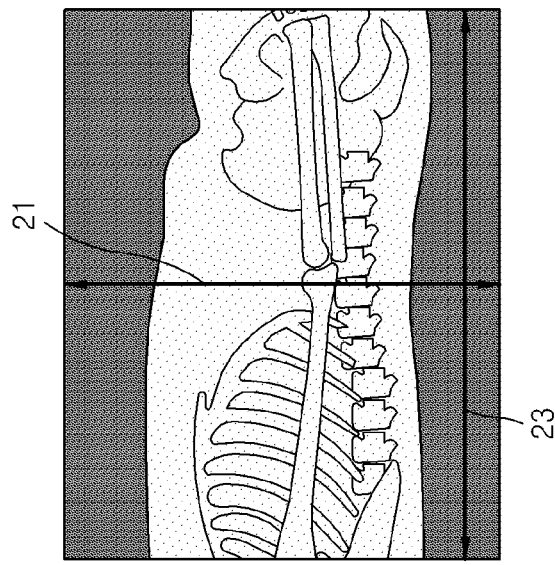
FIGS. 1A and 1B are diagrams for explaining a longitudinal axis length and a transverse axis length.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments.

Thus, it is apparent that exemplary embodiments can be carried out without those specifically defined matters. Also, well-known functions or constructions are not described in detail since they would obscure exemplary embodiments with unnecessary detail.

Expressions such as "at least one of," when preceding a list of elements, modify the entire list of elements and do not modify the individual elements of the list.

It will be understood that when the terms "includes", "comprises", "including", and/or "comprising" when used in this specification, specify the presence of stated elements and/or components, but do not preclude the presence or addition of one or more elements and/or components thereof unless otherwise stated herein. The term "module" as used herein means, but is not limited to, a software or hardware component, such as FPGA or ASIC. A module may advantageously be configured to reside on an addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality of the components and modules may be combined into fewer components and modules or further separated into additional components and modules.

In this specification, an "image" means multi-dimensional data consisting of discrete image elements such as pixels in a two-dimensional (2D) image or voxels in a three-dimensional (3D) image. Examples of the image include medical images of an object that are acquired by using an X-ray machine, a Computed Tomography (CT) system, a Magnetic Resonance Imaging (MRI) system, an ultrasound system, and other medical imaging systems.

An "object" may mean a human body or animal, or any part of the human body or animal. For example, the object may include internal organs, such as the liver, the heart, the uterus, the brain, a breast, and the abdomen, or blood vessels. The object may also include a phantom. A phantom means a material having a volume closely approximating the density and effective atomic number of living tissue and may include a spherical phantom having similar properties to human tissue.

Figure 1A:
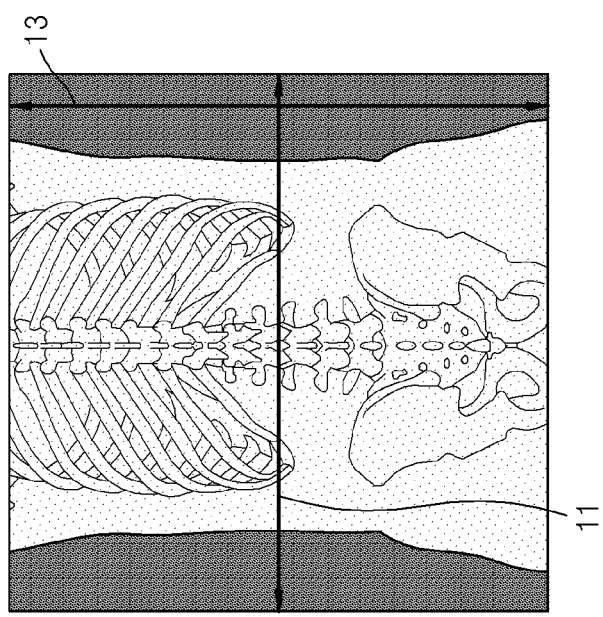

A "user" means a medical expert, and may include, but is not limited to, a doctor, a nurse, a medical technologist, a medical imaging expert, and a medical equipment repair technician. FIGS. 1A and 1B are diagrams for explaining a longitudinal axis length and a transverse axis length;

In this specification, a longitudinal axis length refers to a length in a longitudinal direction of an object. The longitudinal direction of the object may mean a height direction thereof.

A transverse axis length means a length in a width direction of an object. The width direction of the object may be perpendicular to the longitudinal direction thereof.

FIG. 1A illustrates an X-ray image taken when an upper front surface of a lying object, i.e., an X-ray emitter of a CT apparatus, is located at the 12 o'clock position. In FIG. 1A, a transverse axis length of the X-ray image corresponds to a length 11 in a width direction of the object. A longitudinal axis length corresponds to a length 13 in a longitudinal direction of the object.

FIG. 1B illustrates an X-ray image taken when the right side of the lying object, i.e., the X-ray emitter of the CT apparatus, is located at the 3 o'clock position. In FIG. 1B, a transverse axis length of the X-ray image corresponds to a length 21 in a width direction of the object. A longitudinal axis length corresponds to a length 23 in a longitudinal direction of the object.

The transverse axis lengths 11 and 21 of the X-ray images in FIGS. 1A and 1B vary according to transverse axis lengths of X-rays emitted from the X-ray emitter. The longitudinal axis lengths 13 and 23 of the X-ray images vary according to longitudinal axis lengths of X-rays emitted from the X-ray emitter.

Although the longitudinal axis length and the transverse axis length have been described with respect to the X-ray images taken when the X-ray emitter of the CT apparatus is located at the 12 and 3 o'clock positions, a longitudinal axis length and a transverse axis length of X-ray images taken when the X-ray emitter is located at the 1 o'clock position is also obvious to one of ordinary skill in the art.

Figure 2A:
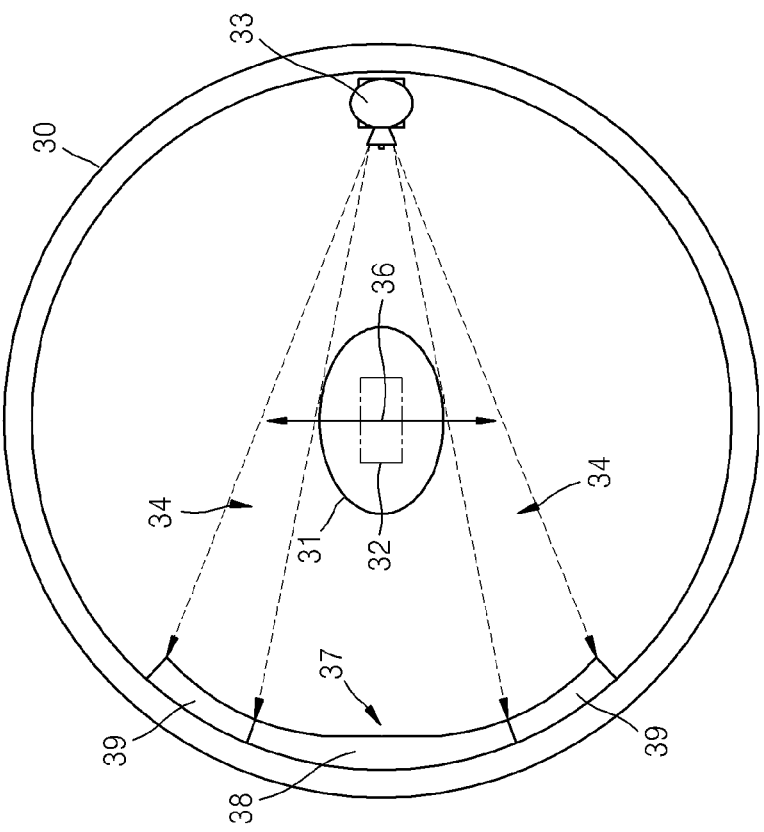
FIGS. 2A and 2B illustrate a CT apparatus for transmitting X-rays to an object.
Figure 2B:
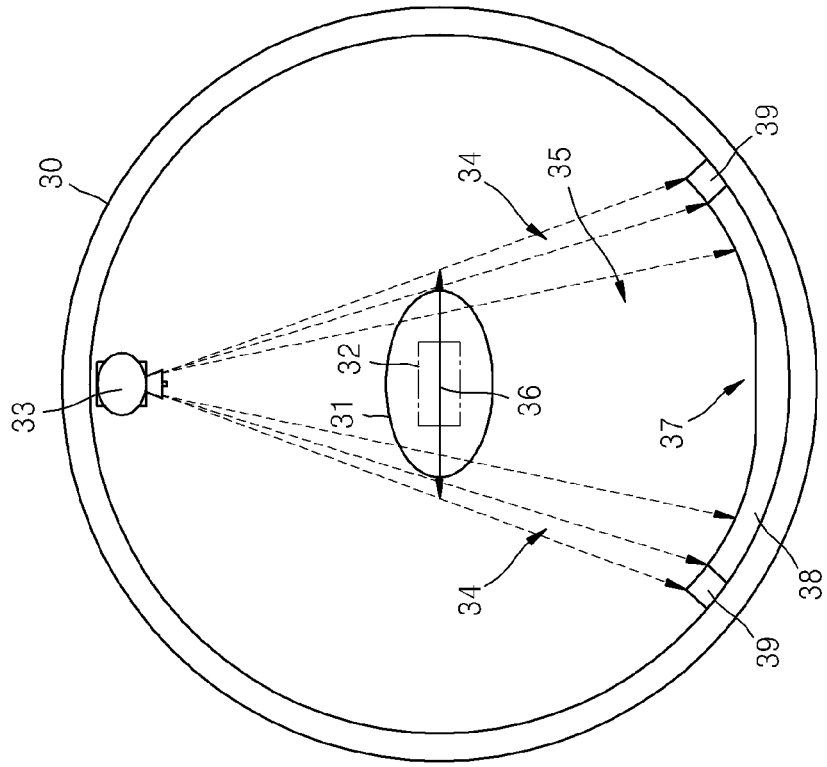

FIGS. 2A and 2B illustrate a CT apparatus for transmitting X-rays to an object.

Referring to FIGS. 2A and 2B, a rotating frame 30 includes an X-ray emitter 33 for emitting an X-ray toward an object 31 and a detector 37 for detecting the X-ray emitted from the X-ray emitter 33. The object 31 is located on a table, and the rotating frame 30 may rotate around the object 31 along a preset rotation path. The X-ray emitter 33 emits an X-ray toward the object 31 as the rotating frame 30 rotates.

The CT apparatus may control a longitudinal axis length of an X-ray by adjusting a distance (not shown) between elements of a longitudinal collimator made of a material that the X-ray is unable to penetrate. In detail, the CT apparatus sets a distance between the elements of the longitudinal collimator for imaging an imaging region of the object 31 and rotates the rotating frame 30 to transmit X-rays to the object 31 through the longitudinal collimator having the elements separated by the set distance. Furthermore, since a longitudinal axis length of the object 31 remains unchanged as the rotating frame 30 rotates, the CT apparatus does not need to change the distance between the elements of the longitudinal collimator while imaging the object 31.

The related art CT apparatus does not include a transverse collimator for adjusting a transverse axis length 36 of an X-ray. In other words, the transverse axis length 36 of the X-ray remains fixed and is mostly set greater than a transverse axis length of the object 31. However, this may shorten the life span of the detector 37.

Referring to FIG. 2A, X-rays 35 passing through the object 31 are attenuated by the object 31, while X-rays 34 not passing through the object 31 are not attenuated by the object 31. Thus, since the X-rays 34 that do not pass through the object 31 strike the detector 37 more strongly than the X-rays 35 that pass therethrough, an outer region 39 of the detector 37, on which the X-rays 34 are incident, continues to be subjected to an increased X-ray flux, compared to a region 38 thereof, on which the X-rays 35 are incident, thereby reducing the life span of the detector 37.

The life span of the detector 37 tends to be reduced more dramatically when an X-ray is emitted from the X-ray emitter 33 at the 12 o'clock position, as shown in FIG. 2A, than when an X-ray is emitted at the 3 o'clock position, as shown in FIG. 2B.

FIG. 2B illustrates emission of an X-ray from the X-ray emitter 33 at the 3 o'clock position. Referring to FIG. 2B, since the object 31 has an oval shape, a traverse axis length 36 of the object 31 is decreased when the X-ray emitter 33 is located at the 3 o'clock position.

Thus, since the amount of the X-rays 34 that do not penetrate the object 31 is increased when the X-ray emitter 33 emits X-rays at the 3 o'clock position, compared to when the X-ray emitter 33 emits the X-rays 34, 35 at the 12 o'clock position, the outer region 39 of the detector 37, where the X-rays 34 are incident, becomes wider than the region 39 thereof shown in FIG. 2A.

Referring to FIGS. 2A and 2B, although an imaging region 32 is set in the object 31, regions other than the imaging region 32 may also be exposed to X-rays 35 because the related art CT apparatus is unable to adjust the transverse axis length 36, thereby increasing the dose of the X-rays accumulated on the object 31.

The related art CT apparatus uses a bowtie filter to adjust the transverse axis length 36 of the X-rays 34, 35. However, the X-rays 34, 35 scattered from the bowtie filter may cause artifacts in an X-ray image. Furthermore, even if a bowtie filter is selected based on when the X-ray emitter 33 is located at the 12 o'clock position, the transverse axis length 36 of the object 31 may be reduced when the X-ray emitter 33 rotates and is located at the 3 o'clock position. Thus, there is still a possibility that the outer region 39 of the detector 37 may be damaged.

Figure 3:
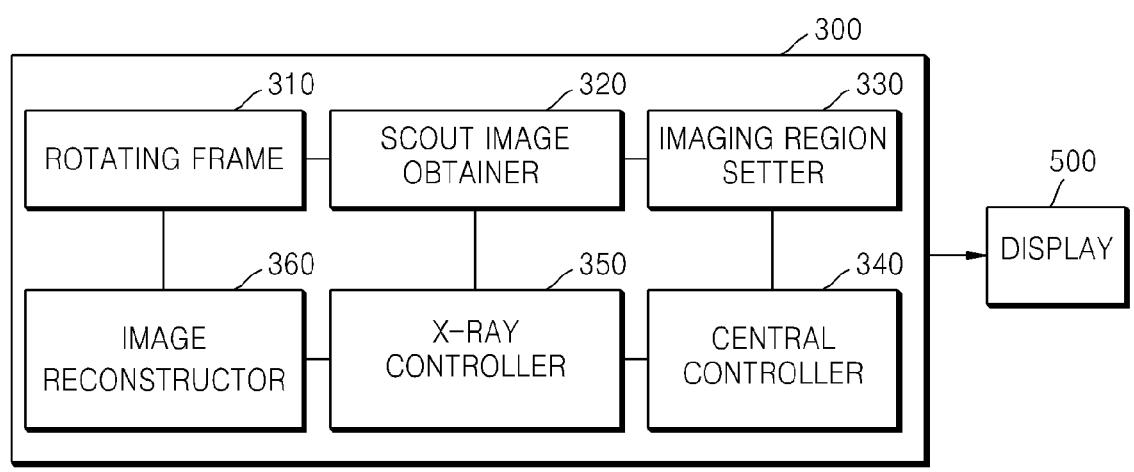
FIG. 3 is a block diagram of a configuration of a CT apparatus according to an exemplary embodiment.

FIG. 3 is a block diagram of a configuration of a CT apparatus 300 according to an exemplary embodiment.

Referring to FIG. 3, the CT apparatus 300 according to an exemplary embodiment includes a rotating frame 310, a scout image obtainer 320, an imaging region setter 330, a central controller 340, an X-ray controller 350, and an image reconstructor 360. The scout image obtainer 320, the imaging region setter 330, the central controller 340, the X-ray controller 350, and the image reconstructor 360 may be realized using a microprocessor.

The rotating frame 310 is connected to an X-ray emitter (not shown) for emitting X-rays toward an object and a detector (not shown) for detecting the X-rays emitted by the X-ray emitter. The rotating frame 310 may also rotate about a predetermined rotary axis along a preset rotation path. While the rotating frame 310 rotates around the object, the X-ray emitter emits X-rays toward the object, and the detector detects the X-rays emitted by the X-ray emitter to generate projection data.

The X-ray emitter may be connected to a longitudinal collimator (not shown) and a transverse collimator (not shown). A longitudinal axis length of an X-ray may be adjusted by controlling a distance between two collimator elements in the longitudinal collimator. Similarly, a transverse axis length of the X-ray may be adjusted by controlling a distance between two collimator elements of the transverse collimator.

Each of the longitudinal collimator and the transverse collimator may include two collimator elements made of a material that an X-ray is unable to penetrate and blocks X-rays emitted by the X-ray emitter. As the distances between the two collimator elements of the longitudinal collimator and the transverse collimator decrease, the longitudinal axis length and the transverse axis length of an X-ray decrease, respectively.

The scout image obtainer 320 acquires scout images of the object based on images of the object that are taken at a plurality of points along the rotation path of the rotating frame 310. A scout image refers to an image acquired prior to a CT scan in order to set an imaging protocol or an imaging region, or inject a contrast medium.

When the X-ray emitter emits X-rays toward the object from a plurality of points and the detector detects the X-rays emitted from the plurality of points by the X-ray emitter to generate projection data for the object, the scout image obtainer 320 may acquire projection images of the object that are generated based on the projection data as scout images of the object.

Alternatively, if cross-sectional images of the object are reconstructed from the projection data, the scout image obtainer 320 may acquire the cross-sectional images of the object as scout images of the object.

As another example, when the CT apparatus 300 further includes a camera (not shown) for photographing the object from a plurality of viewpoints, the scout image obtainer 320 may acquire images of the object that are taken by the camera as scout images of the object. The camera may include a black-and-white camera, a color camera, a video camera, an infrared camera, or a depth camera.

The imaging region setter 330 sets an imaging region 32 of the object in scout images of the object that are acquired by the scout image obtainer 320.

The imaging region setter 330 may set an imaging region 32 in scout images of the object based on a user input. For example, if the user selects a region in the scout images, the imaging region setter 330 may set the selected region as an imaging region 32.

The central controller 340 determines an outline of a transverse axis length 36 of an imaging region 32 based on transverse axis lengths 36 of the imaging region 32 set in scout images. The outline of the transverse axis length 36 of the imaging region 32 contains information about transverse axis lengths 36 of the imaging region 32 at an angle at which the rotating frame 310 rotates. For example, the outline may include information about transverse axis lengths 36 of the imaging region 32 when the rotating frame 310 rotates at angles of 30° and 60°, respectively. A method of determining an outline will be described below with reference to FIGS. 4A and 4B.

The central controller 340 may determine a longitudinal axis length of an imaging region 32 of one of the scout images of the object. Since a longitudinal axis length of the object remains unchanged during rotation of the rotating frame 310, the longitudinal axis length may be determined by using one scout image.

The central controller 340 also acquires information about a position of an imaging region 32 set in the scout images of the object. For example, if the heart of the object is set as an imaging region 32 by using the scout images of the object, the left side of the chest of the object may be obtained as information about the position of the imaging region 32.

The X-ray controller 350 controls an X-ray emitted from the X-ray emitter toward an object by adjusting a distance between the two collimator elements of the transverse collimator according to an outline determined by the central controller 340. In detail, the X-ray controller 350 determines the distance between the two collimator elements of the transverse collimator corresponding to the outline determined by the central controller 340 and adjusts the distance during rotation of the rotating frame 310 to control a transverse axis length of the X-ray.

Furthermore, when the central controller 340 determines a longitudinal axis length of an imaging region 32, the X-ray controller 350 may control a transverse axis length and a longitudinal axis length of the X-ray emitted toward the object by adjusting distances between the collimator elements of the transverse collimator and between the collimator elements of the longitudinal collimator in consideration of both the outline and the longitudinal axis length, respectively.

When the central controller 340 acquires information about a position of the imaging region 32, the X-ray controller 350 may also control the X-ray in consideration of the outline and the information about the position of the imaging region 32. For example, if the left side of the chest of the object is set as the information about the position of the imaging region 32, the X-ray controller 350 may control the transverse collimator so that the X-ray is emitted toward the left side of the chest by controlling the transverse axis length 36 of the X-ray according to the outline.

When the detector detects X-rays controlled by the X-ray controller 350 to generate X-ray projection data for the object, the image reconstructor 360 reconstructs a cross-sectional X-ray image of the object based on the X-ray projection data. Alternatively, the image reconstructor 360 may generate a projection image of the object from the X-ray projection data.

The CT apparatus 300 according to an exemplary embodiment is configured to emit X-rays corresponding to a transverse axis length 36 of an imaging region 32 of an object, thereby preventing a decrease in the life span of an outer region of the detector. The CT apparatus 300 is also configured to only emit X-rays in a range suitable for scanning the imaging region 32 of the object, thereby reducing the amount of X-rays accumulated by the object.

Furthermore, unlike a related art CT apparatus for imaging an object by using a bowtie filter suitably determined in consideration of an imaging region 32 of the object, the CT apparatus 300 according to an exemplary embodiment requires a single bowtie filter because a transverse axis length 36 of an X-ray may be adjusted by a transverse collimator.

In addition, when a particular imaging region 32 such as the heart is to be imaged, a related art CT apparatus requires movement by the object so that the heart is situated at the center of an X-ray region or a table supporting the object. However, the CT apparatus 300 according to an exemplary embodiment is configured to control the direction in which the X-ray is emitted by acquiring information about a position of an imaging region 32, thereby eliminating the need for moving by the object or the table.

A method of determining an outline will now be described with reference to FIGS. 4A and 4B.

When the imaging region setter 330 sets an imaging region 32 in a first scout image and a second scout image acquired from images of an object that are taken in the 12 o'clock direction and 3 o'clock direction of the rotating frame 310, respectively, the central controller 340 first determines transverse axis lengths 36 of the imaging region 32 set in the first and second scout images.

Figure 4A:
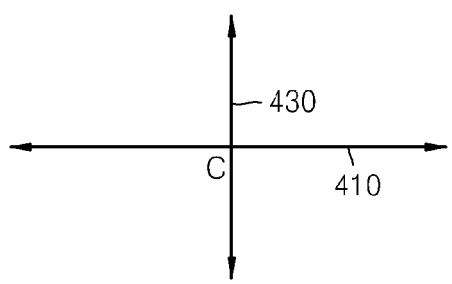
FIGS. 4A and 4B illustrate a method of determining an outline of a transverse axis length of an imaging region.

FIG. 4A illustrates a transverse axis length 410 of a first scout image and a transverse axis length 430 of a second scout image.

Referring to FIGS. 3 and 4A, the central controller 340 applies ellipse mapping to the transverse axis lengths 410 and 430 of the first and second scout images, based on a central point C of the imaging region 32 set in the first and second scout images. A length of a diameter passing through the central point C of an ellipse mapped to the transverse axis lengths 410 and 430 of the first and second scout images corresponds to a transverse axis length of an imaging region 32 according to a rotation angle of the rotating frame 310.

Figure 4B:
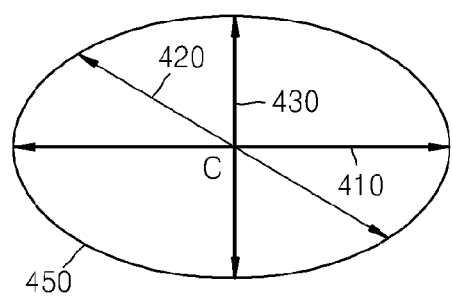

FIG. 4B illustrates an ellipse 450 mapped to a transverse axis length 410 of a first scout image and a transverse axis length 430 of a second scout image. Referring to FIGS. 3 and 4B, the transverse axis length 410 of the first scout image represents a transverse axis length of an imaging region 32 in the 12 o'clock direction of the rotating frame 310, i.e., at a rotation angle of 0°. The transverse axis length 430 of the second scout image represents a transverse axis length of the imaging region 32 in the 3 o'clock direction of the rotating frame 310, i.e., at a rotation angle of 90°. A transverse axis length of the imaging region 32 at a rotation angle of 45° corresponds to a diameter 420 of the ellipse 450 when the transverse axis length 410 at a rotation angle of 0° rotates by 45°.

The central controller 340 may determine the ellipse 450 mapped to the transverse axis lengths 410 and 430 of the first and second scout images as an outline. Alternatively, the central controller 340 may determine an ellipse that is larger than the ellipse 450 by a preset size as an outline. In this case, the CT apparatus 300 acquires a cross-sectional image including a region larger than the imaging region 32 of the object, thereby facilitating a diagnosis by a user.

The X-ray controller 350 may adjust a distance between the collimator elements of the transverse collimator according to the outline generated by the central controller 340 as the rotating frame 310 rotates 360°.

Although not shown in FIG. 3, the CT apparatus 300 according to an exemplary embodiment may further include a display 500 for displaying scout images of the object, transverse axis lengths of an imaging region 32 set in the scout images, and an outline determined by the central controller 340.

Figure 5:
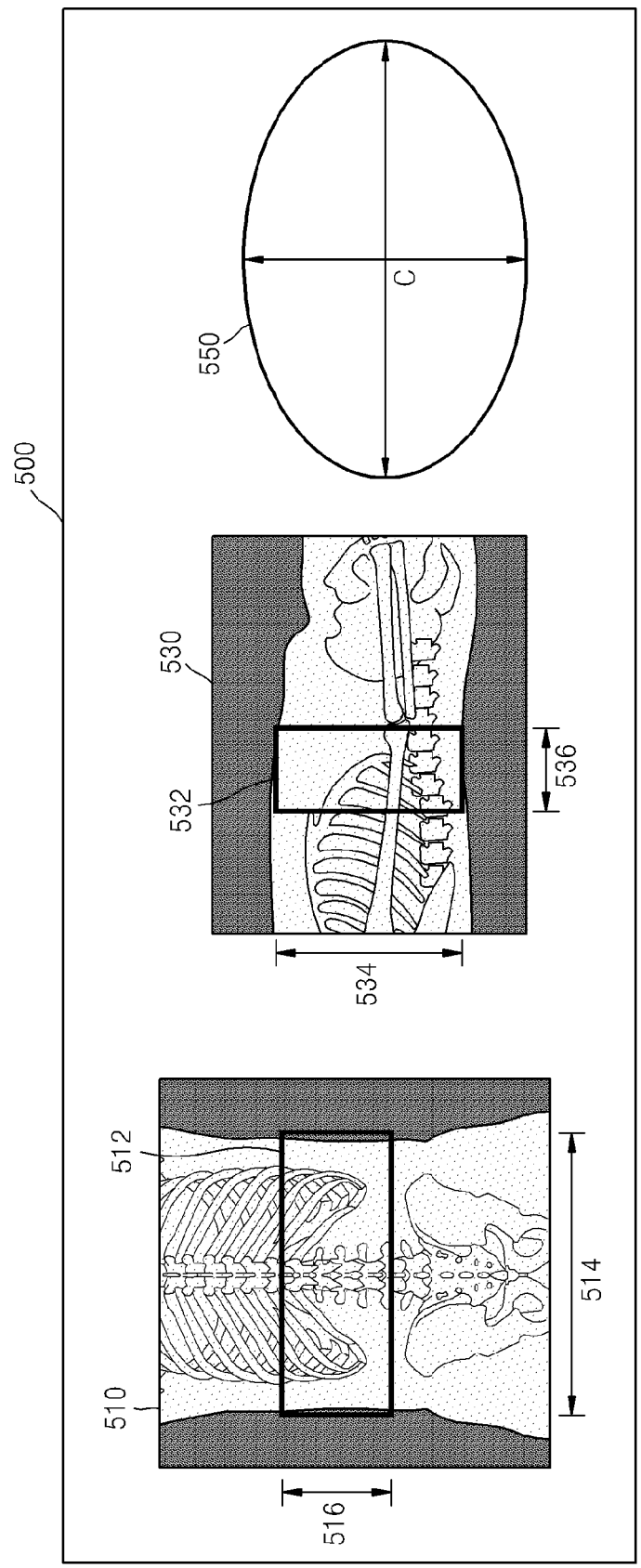
FIG. 5 illustrates scout images, imaging regions, and an outline displayed on a display of a CT apparatus according to an exemplary embodiment.

FIG. 5 illustrates first and second scout images 510 and 530, transverse axis lengths 514 and 534 of imaging regions 512 and 532, and an outline 550 displayed on a display 500 of a CT apparatus according to an exemplary embodiment.

Referring to FIGS. 3 and 5, the display 500 may display the first and second scout images 510 and 530 of an object that are acquired by the scout image obtainer 320. A user may set the imaging regions 512 and 532 for the first and second scout images 510 and 530 displayed on the display 500. When the imaging regions 512 and 532 are set for the first and second scout images 510 and 530, respectively, the display 500 may display the transverse axis lengths 514 and 534 of the imaging regions 512 and 532 set in the first and second scout images 510 and 530, respectively, as numerical values. The display 500 may also display longitudinal axis lengths 516 and 536 of the imaging regions 512 and 532 set in the first and second scout images 510 and 530, respectively, as numerical values.

The display 500 may display the outline 550 determined by the central controller 340 so as to provide in advance the user with information about how an imaging region 512, 532 of the object will be imaged.

The user may determine whether to image the object according to the displayed outline 550. When the central controller 340 receives a user input for changing the outline 550, the central controller 340 may change the outline 550 according to the user input. For example, if the user expands the outline 550, the central controller 340 may determine an outline obtained by expanding the outline 550 as an outline of a transverse axis length of an imaging region. In this case, the X-ray controller 350 may control an X-ray emitted toward the object by adjusting a distance between collimator elements of the transverse collimator according to the outline obtained by changing the outline 550.

According to CT apparatuses, a position or temperature of an X-ray emitter may be changed as the rotating frame 310 rotates and tilts, thereby causing a focal point of an X-ray emitted toward an object to deviate from an original set point.

On the other hand, in the CT apparatus 300 according to an exemplary embodiment, when a focal point of an X-ray that is controlled according to an outline 550 for emission toward an object deviates from an original set point, the focal point of the X-ray may be changed back to the original set point, as described below with reference to FIG. 6.

Figure 6:
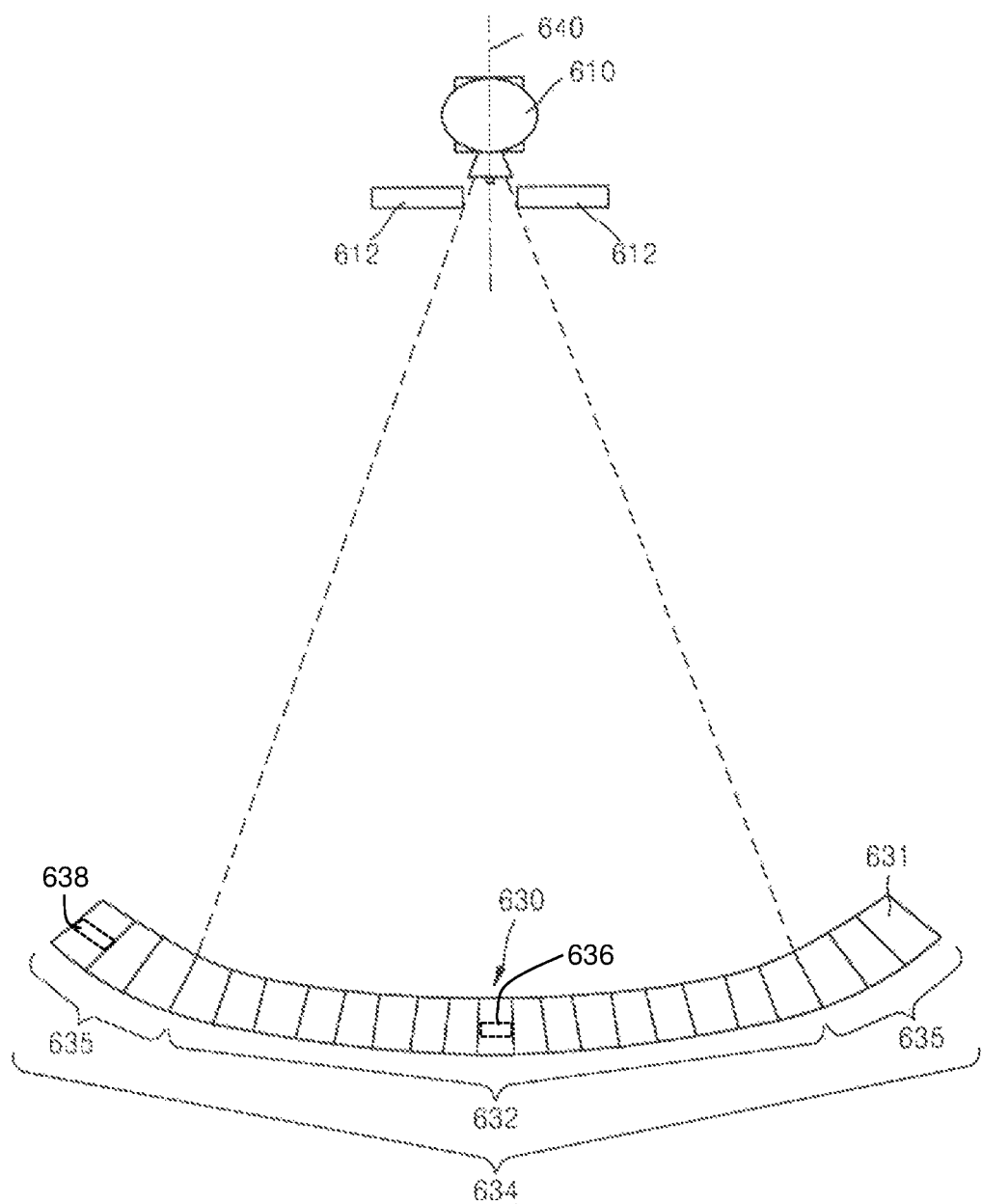
FIG. 6 illustrates a plurality of detector elements in a detector.

FIG. 6 illustrates a plurality of detector elements in a detector 630.

Referring to FIGS. 3 and 6, the detector 630 detects X-rays emitted by an X-ray emitter 610 and includes the plurality of detector elements 631. Each of the detector elements 631 detects an X-ray that has been emitted by the X-ray emitter 610 and passed through transverse collimator having collimator elements 612 and generates projection data for an object.

The central controller 340 determines first detector elements 632 corresponding to an outline 550 among the plurality of detector elements 631 as well as second detector elements 634 for detecting X-rays of which emission is controlled by the X-ray controller 350.

Since the central controller 340 is aware of a transverse axis length and a direction of an X-ray emitted by the X-ray emitter 610, the central controller 340 may determine the first detector elements 632 which are expected to detect X-rays emitted by the X-ray emitter 610. The central controller 340 may also determine the second detector elements 634 that actually detect X-rays whose emission is controlled according to the outline 550.

The central controller 340 compares the first detector elements 632 with the second detector elements 634 to determine whether they are the same as one another. If the first detector elements 632 are the same as the second detector elements 634, this means that a position of a focal point of an X-ray emitted from the X-ray emitter 610 does not deviate from a preset focal point of the X-ray. On the other hand, if the first detector elements 632 and the second detector elements 634 are different from one another (e.g., third detector elements indicated by a reference numeral 635), it means that the position of the focal point of the X-ray emitted from the X-ray emitter 610 deviates from the preset focal point of the X-ray.

The X-ray controller 350 changes a position of a focal point of an X-ray based on the comparison result obtained by the central controller 340. In detail, to do so, the X-ray controller 350 may change a position of the X-ray emitter 610 or adjust a distance between the collimator elements 612. The focal point of the X-ray may correspond to a central axis 640 of the X-ray emitter 610.

The central controller 340 and the X-ray controller 350 may determine a position of the focal point of the X-ray and change the position of the focal point at different times. For example, the central controller 340 and the X-ray controller 350 may determine and change the position of the focal point at the time between first and second rotations of the rotating frame 310 or at predetermined time intervals during rotation of the rotating frame 310.

Each of the detector elements 631 shown in FIG. 6 may include an electrical signal generator for generating an electrical signal corresponding to the intensity of an X-ray, an analog-to-digital (A/D) converter for converting the electrical signal generated by the electrical signal generator into a digital electrical signal, and a memory for storing the digital electrical signal. The electrical signal generator may include a scintillator for primarily converting an X-ray into light. An electrical signal generated by the electrical signal generator or a digital electrical signal generated by the A/D converter may correspond to projection data for an object.

The memory has a limited storage capacity to generally store about 10 seconds of projection data.

When the first detector elements 632 detect X-rays emitted from the X-ray emitter 610, projection data generated by the detected X-rays may be stored in a memory (reference numeral 636) in each of the first detector elements 632 or a memory (reference numeral 638) in each of the third detector elements 635. This may increase the available capacity of the memory of the first detector element 632. In FIG. 6, only one of the first detector elements 632 and only one of the third detector elements 635 are illustrated as having a corresponding memory, for convenience of description. However, each of the first detector elements 632 and each of the third detector elements 635 has a corresponding memory.

That is, the CT apparatus 300 according to an exemplary embodiment is configured to increase the available capacity of memory available for the first detector element 632 and store projection data that lasts for a long time, thereby reducing a cut-off of an X-ray image.

Figure 7A:
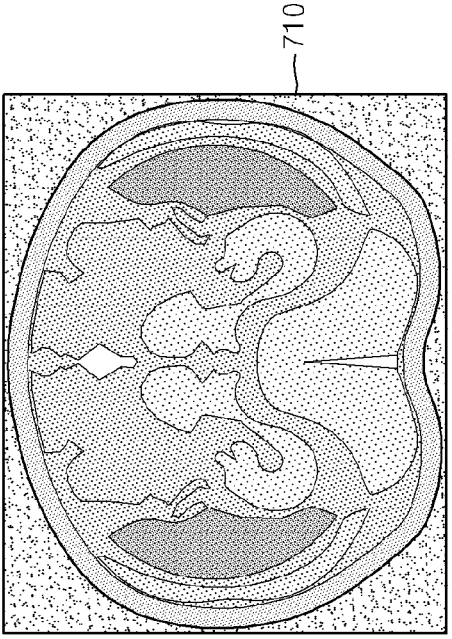
FIG. 7A illustrates a first cross-sectional X-ray image of an object.
Figure 7B:
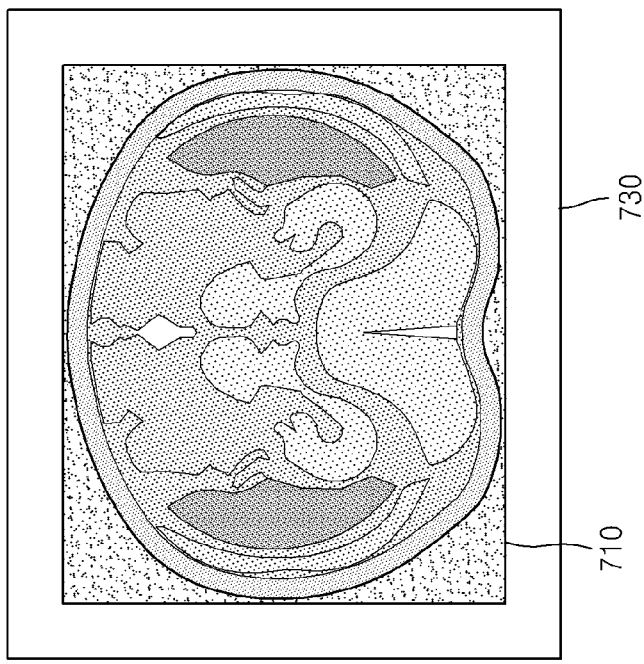
FIG. 7B illustrates a region having a preset size on which the cross-sectional X-ray image of the object is displayed.
Figure 7C:
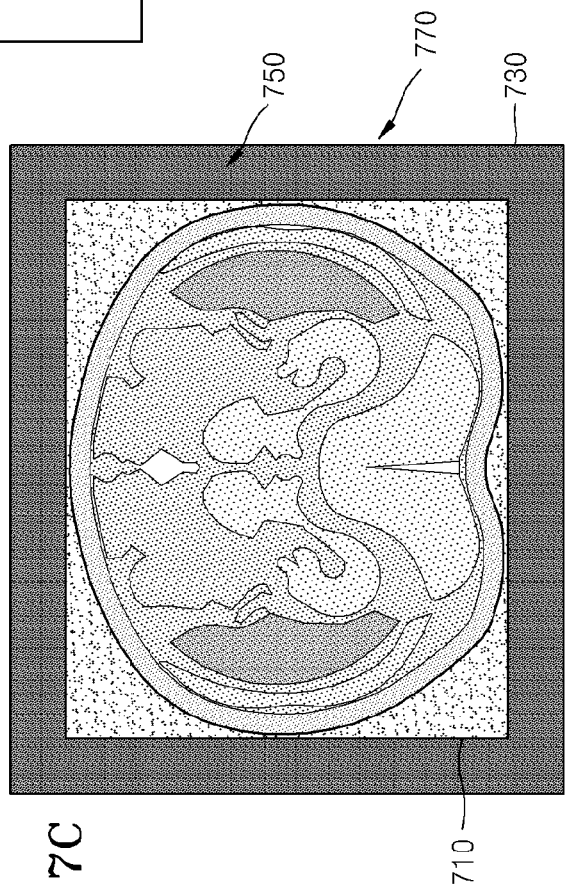
FIG. 7C illustrates a second cross-sectional X-ray image of the object.

FIG. 7A illustrates a first cross-sectional X-ray image 710 of an object, FIG. 7B illustrates a region 730 having a preset size on which the first cross-sectional X-ray image 710 of the object is displayed, and FIG. 7C illustrates a second cross-sectional X-ray image 770 of the object.

As described above, the CT apparatus according to an exemplary embodiment is configured to emit an X-ray corresponding to a longitudinal axis length and a transverse axis length of an imaging region 512, 532 set in scout images of an object. Thus, a cross-sectional X-ray image generated by the image reconstructor 360 may vary depending on a size of the imaging region set in the scout images of the object.

According to a related art CT apparatus, a cross-sectional X-ray image generated by X-rays that pass through air other than the object to the detector has a brightness corresponding to an attenuation coefficient of air that is expressed in Hounsfield units (HU). The user may compare a color of a cross-sectional X-ray image generated by X-rays that pass through air to the detector with a color of a cross-sectional X-ray image generated by X-rays that pass through the object to the detector to determine whether the object has a lesion.

However, in the CT apparatus 300 according to an exemplary embodiment, since an X-ray controlled to correspond to a transverse axis length 514, 534 of an imaging region 512, 532 does not pass through air to the detector, a color corresponding to HU of air is not represented in the first cross-sectional X-ray image 710 generated by the CT apparatus 300.

FIG. 7A illustrates the first cross-sectional X-ray image 710 of an object that is generated from X-rays controlled according to an outline 550 for emission toward the object. The first cross-sectional X-ray image 710 does not have a color corresponding to the HU of air.

The image reconstructor 360 may represent the first cross-sectional X-ray image 710 in the region 730 having a preset size. The region 730 shown in FIG. 7B may be set to have a size of a cross-sectional X-ray image generated by a related art CT apparatus.

The image reconstructor 360 may display the remaining portion 750 of the region 730, other than a portion where the first cross-sectional X-ray image 710 is displayed, by a predetermined color to thereby generate the second cross-sectional X-ray image 770 shown in FIG. 7C. The predetermined color may include a color corresponding to HU of air.

The user may compare a color of the second cross-sectional X-ray image 770 corresponding to HU of air with a color corresponding to HU of the object to more easily determine whether the object has a lesion.

FIG. 8 is a flowchart of a method of controlling an X-ray in the CT apparatus 300, according to an exemplary embodiment. Referring to FIG. 8, the method of controlling an X-ray in the CT apparatus 300, according to an exemplary embodiment, includes operations performed by the CT apparatus 300 in a time series. Thus, although omitted hereinafter, the descriptions of the CT apparatus 300 of FIG. 3 apply to the method of controlling an X-ray in the CT apparatus 300 illustrated in FIG. 8.

Referring to FIGS. 3 and 8, the CT apparatus 300 acquires scout images of an object by using images of the object that are taken at a plurality of points along a rotation path of the rotating frame 310 (operation S810).

The CT apparatus 300 then sets an imaging region 512, 532 of the object in the scout images 510, 530 of the object (operation S820).

The scout images 510, 530 may include projection images of the object that are generated from X-rays that are emitted from a plurality of points toward the object and detected by a detector 630, cross-sectional images 710, 770 of the object that are reconstructed from the projection data, or images of the object photographed by a camera from a plurality of points.

The CT apparatus 300 determines an outline 550 of transverse axis lengths 514, 534 of an imaging region 512, 532 along the rotation path of the rotating frame 310 based on transverse axis lengths 514, 534 of the imaging region 512, 532 set in the scout images 510, 530 of the object (operation S830). Since the method of determining an outline 550 has been described above with reference to FIG. 4, a detailed description thereof will be omitted here.

The CT apparatus 300 controls an X-ray emitted toward the object by adjusting a distance between collimator elements 612 of the transverse collimator according to the outline (operation S840).

The CT apparatus 300 reconstructs a first cross-sectional X-ray image 710 of the object based on X-ray projection data generated by detecting the X-ray controlled according to the outline (operation S850).

To change the reconstructed first cross-sectional X-ray image 710 to conform to a size and appearance of a cross-sectional X-ray image generated by a related art CT apparatus, the CT apparatus 300 represents the first cross-sectional X-ray image 710 in a region 730 having a preset size, and displays the remaining portion 750 of the region 730, other than a portion on which the first cross-sectional X-ray image 710 is represented, in a predetermined color to thereby generate a second cross-sectional X-ray image 770 of the object.

Figure 9:
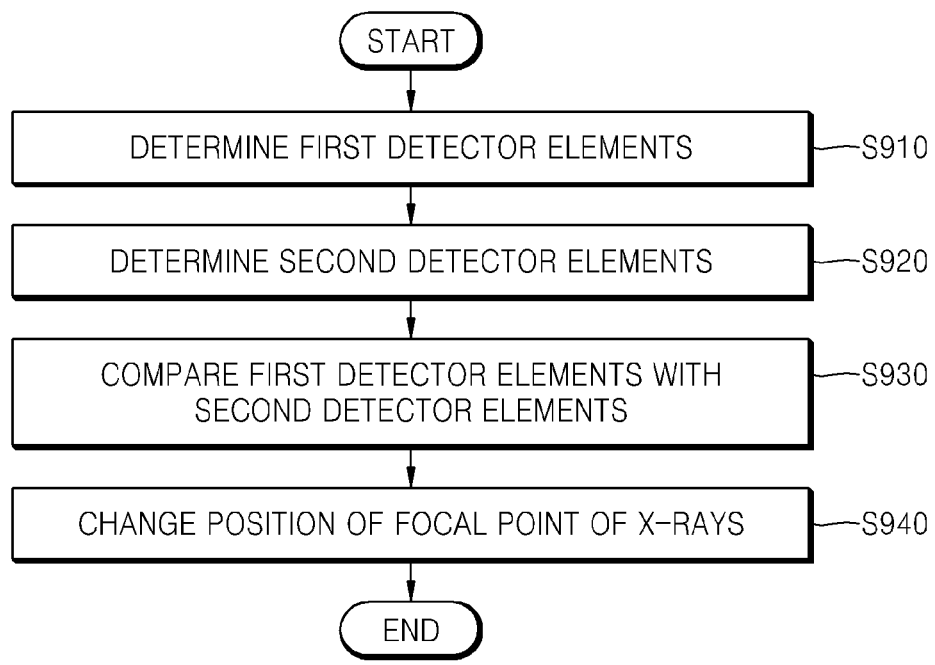
FIG. 9 is a flowchart of a method of changing a position of a focal point of an X-ray, according to an exemplary embodiment.

FIG. 9 is a flowchart of a method of changing a position of a focal point of an X-ray when the position of the focal point of the X-ray emitted toward an object deviates from a preset focal point of the X-ray, according to an exemplary embodiment.

The CT apparatus 300 determines first detector elements 632 corresponding to the outline 550 among a plurality of detector elements 631 in a detector 630 of the CT apparatus 300 (operation S910). The first detector elements 632 include detector elements 631 that are expected to detect X-rays of which emission is controlled according to the outline 550.

The CT apparatus 300 determines second detector elements 634 that detect X-rays whose emission is controlled according to the outline 550 among the plurality of detector elements 631 (operation S920). The second detector elements 634 include detector elements 631 that actually detect the X-rays.

The CT apparatus 300 compares the first detector elements 632 with the second detector elements 634 (operation S930).

The CT apparatus 300 changes a position of a focal point of an X-ray emitted toward the object based on the comparison result, in operation S940.

Figure 10:
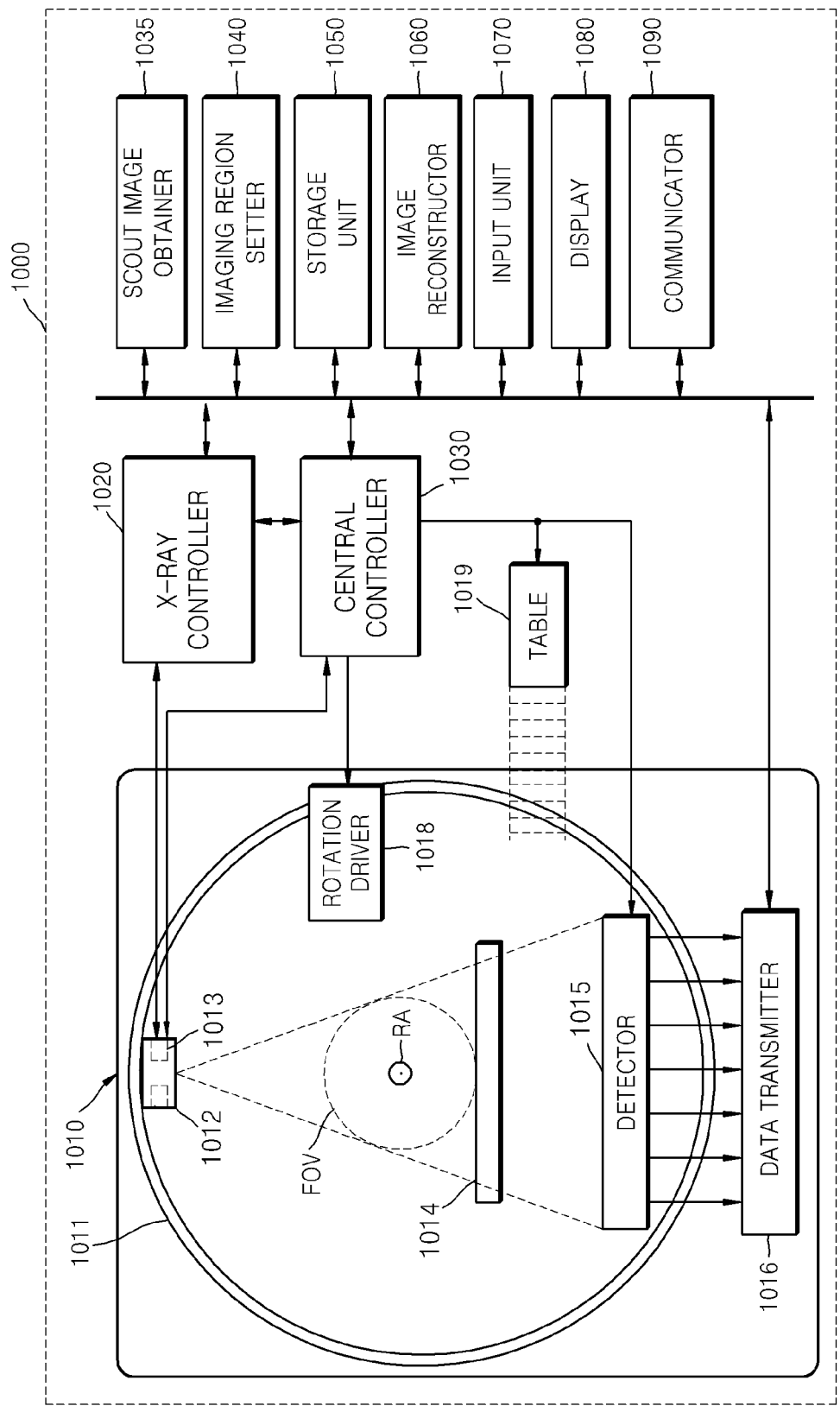
FIG. 10 illustrates a configuration of a CT apparatus according to another exemplary embodiment.

FIG. 10 illustrates a configuration of a CT apparatus 1000 according to another exemplary embodiment.

Referring to FIG. 10, the CT apparatus 1000 according to an exemplary embodiment includes a gantry 1010, a table 1019, an X-ray controller 1020, a central controller 1030, a scout image obtainer 1035, an imaging region setter 1040, a storage unit 1050, an image reconstructor 1060, an input unit 1070, a display 1080, and a communicator 1090.

The object may be placed on the table 1019. The table 1019 may be movable in a predetermined direction (e.g., at least one of up, down, left, and right directions), and movement thereof may be controlled by the central controller 1030.

The gantry 1010 may include a rotating frame 1011, an X-ray emitter 1012, a detector 1015, a data transmitter 1016, and a rotation driver 1018.

In detail, the gantry 1010 may include the rotating frame 1011 having a ring shape rotatable about a predetermined rotation axis (RA). The rotating frame 1011 may also be disc-shaped.

The rotating frame 1011 may include the X-ray emitter 1012 and the detector 1015 disposed opposite each other to have a predetermined field of view (FOV). The rotating frame 1011 may further include an anti-scatter grid 1014 disposed between the X-ray emitter 1012 and the detector 1015.

An X-ray that reaches the detector 1015 (or a photosensitive film) includes attenuated primary radiation for creating a useful image and scattered radiation that degrades the quality of an image. The anti-scatter grid 1014 is disposed between a patient and the detector 1015 (or the photosensitive film) and transmits most of the attenuated primary radiation and attenuates the scattered radiation.

For example, the anti-scatter grid 1014 is formed from alternate stacking of strips of lead foil and interspace material such as a solid polymer material or a solid polymer and a fiber composite material. However, the anti-scatter grid 1014 is not limited thereto and may have other forms.

The rotating frame 1011 receives a drive signal from the rotation driver 1018 and rotates the X-ray emitter 1012 and the detector 1015 at a predetermined rotational speed. The rotating frame 1011 may receive a drive signal and power from the rotation driver 1018 through a slip-ring (not shown) by using a contact method. The rotating frame 1011 may also receive a drive signal and power from the rotation driver 1018 over a wireless network.

The X-ray emitter 1012 may receive a voltage and a current through a power distribution unit (PDU), the slip-ring, and a high voltage generator (not shown) to generate X-rays for emission. When the high-voltage generator applies a predetermined voltage (hereinafter, referred to as a tube voltage) to the X-ray emitter 1012, the X-ray emitter 1012 may generate X-rays having a plurality of energy spectra corresponding to the predetermined tube voltage. The X-rays generated by the X-ray emitter 1012 may be radiated in a predetermined pattern by a transverse collimator 1013 and a longitudinal collimator (not shown).

The detector 1015 may be disposed opposite the X-ray emitter 1012 and include a plurality of detector elements.

Each of the detector elements may detect an X-ray generated by the X-ray emitter 1012 and transmitted through the object and generate an electrical signal corresponding to the intensity of the X-ray. The detector element may include an electrical signal generator for generating an electrical signal by using an X-ray, an A/D converter for converting an electrical signal into a digital electrical signal, and a memory for storing the digital electrical signal.

The electrical signal generator may have two operation modes, i.e., an indirect mode in which the X-ray is first converted into light and then into an electrical signal, and a direct mode in which the X-ray is converted directly into an electrical signal. An indirect mode electrical signal generator may include a scintillator, and a direct mode electrical signal generator may include a photon counting detector.

Projection data stored in a memory of each detector element may be provided to the image reconstructor 1060 via the data transmitter 1016. The projection data may be transmitted to the image reconstructor 1060 through the data transmitter 1016 in a wired or wireless manner.

The central controller 1030 may control an operation of each element in the CT apparatus 1000. For example, the central controller 1030 may control operations of the table 1019, the rotation driver 1018, the scout image obtainer 1035, the image reconstructor 1060, the input unit 1070, the display 1080, and the communicator 1090.

The central controller 1030 may also determine an outline of transverse axis lengths of an imaging region along the rotation path of the rotating frame 1011, based on transverse axis lengths of the imaging region set in scout images of the object that are acquired from a plurality of points on the rotation path of the rotating frame 1011.

The central controller 1030 may determine a longitudinal axis length of an imaging region of one of the scout images of the object.

The X-ray controller 1020 may control a transverse axis length of an X-ray emitted toward the object by adjusting a distance between elements of the transverse collimator 1013 according to the outline determined by the central controller 1030 during rotation of the rotating frame 1011.

The X-ray controller 1020 may also control a longitudinal axis length of the X-ray by adjusting a distance between elements of the longitudinal collimator according to the longitudinal axis length determined by the central controller 1030.

The scout image obtainer 1035 may acquire scout images of the object by using images of the object that are taken at a plurality of points along the rotation path of the rotating frame 1011.

The imaging region setter 1040 may set an imaging region of the object in the scout images of the object. A scout image refers to an image acquired prior to a CT scan in order to set an imaging protocol or an imaging region, or inject a contrast medium.

The image reconstructor 1060 may perform pre-processing on projection data received through the data transmitter 1016.

For example, the pre-processing may include a sensitivity non-uniformity correction process and a process for correcting signal loss due to a rapid decrease in signal intensity or the presence of an X-ray absorber such as metals.

The projection data may be stored in the storage unit 1050 together with imaging conditions data acquisition such as X-ray emission voltages and imaging angles.

The projection data may be a set of data values corresponding to the intensities of X-rays passing through the object. For convenience of explanation, a set of projection data acquired simultaneously at the same imaging angle is hereinafter referred to as a projection data set.

The storage unit 1050 may include at least one storage medium from among a flash memory-type storage medium, a hard disk-type storage medium, a multimedia card micro-type storage medium, card-type memories (e.g., an SD card, an XD memory, and the like), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, a magnetic disc, and an optical disc.

The image reconstructor 1060 may also reconstruct a cross-sectional X-ray image of the object based on the projection data set. The cross-sectional X-ray image may be a 3D image. In other words, the image reconstructor 1060 may generate a 3D X-ray image of the object based on the projection data set by using a reconstruction technique such as cone beam reconstruction.

The image reconstructor 1060 may also represent the cross-sectional X-ray image of the object in a region having a preset size, and displays the remaining portion of the region, other than a portion on which the cross-sectional X-ray image is represented, in a predetermined color to thereby generate a second cross-sectional X-ray image of the object.

External inputs such as X-ray imaging conditions and image processing conditions may be received through the input unit 1070. For example, the X-ray imaging conditions may include a plurality of X-ray emission voltages, settings of energy values of a plurality of X-rays, imaging protocol settings, selection of image reconstruction methods, FOV settings, number of slices, slice thicknesses, settings of parameters for image post-processing. The image processing conditions may include resolutions of images, settings of attenuation coefficients of images, and settings of an image combination ratio.

The input unit 1070 may include a device for receiving a predetermined input from the outside. For example, the input unit 1070 may include a microphone, a keyboard, a mouse, a joystick, a touch pad, a touch pen, a voice recognition device, and a gesture recognition device.

The display 1080 may display a cross-sectional X-ray image reconstructed by the image reconstructor 1060. The display 1080 may also display scout images, transverse axis lengths of an imaging region, and an outline of transverse axis lengths.

The transmission and reception of data and power among the above-described elements may be performed by using at least one selected from wired communication, wireless communication, and optical communication.

The communicator 1090 communicates with an external device or external medical device via a network, as described below with reference to FIG. 11.

Figure 11:
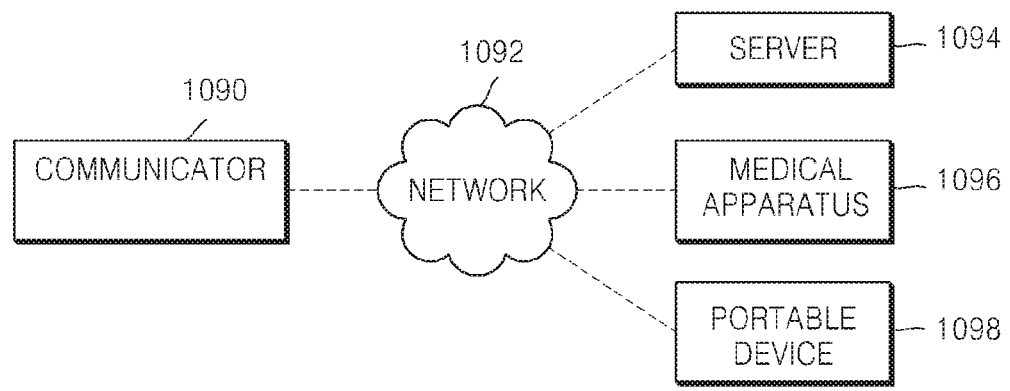
FIG. 11 illustrates a communicator in the CT apparatus of FIG. 10.

FIG. 11 illustrates the communicator 1090 in the CT apparatus 1000 of FIG. 10.

The communicator 1090 may exchange data with a hospital server or other medical devices within a hospital via a picture archiving and communication system (PACS) and perform data communication according to the Digital Imaging and Communications in Medicine (DICOM) standard.

Referring to FIG. 11, the communicator 1090 is connected to a network 1092 by wires or wirelessly to communicate with a server 1094, an external medical apparatus 1096, or an external portable device 1098.

In detail, the communicator 1090 may transmit or receive data related to diagnosis of an object through the network 1092. For example, the communicator 1090 may transmit or receive medical images generated by the external medical apparatus 1096 such as a CT, an MRI, or an X-ray imaging system. The communicator 1090 may also receive a patient's diagnosis history or medical treatment plan from the server 1094 and use the diagnosis history or the medical treatment plan for the diagnosis of the patient. In addition to communicating with the server 1094 and the external medical apparatus 1096 within a hospital, the communicator 1090 may perform data communication with the external portable device 1098 such as a doctor or client's mobile phone, personal digital assistant (PDA), and notebook computer.

The communicator 1090 may also transmit information about an error in a CT system or medical image quality to a user and receive feedback from the user as a response to the information over the network 1092.

The communicator 1090 may include one or more components that enable communication with external devices. For example, the communicator 1090 may include a local area communicator, a wired communicator, and a wireless communicator.

The exemplary embodiments can be recorded as programs that can be executed on a computer and be implemented through computers which execute the programs using a computer-readable recording medium.

Examples of the computer-readable recording medium include recording media such as magnetic storage media (e.g., ROM, floppy disks, hard disks, etc.), and optical recording media (e.g., CD-ROMs or DVDs).

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A method of controlling an X-ray in a computed tomography (CT) apparatus, the method comprising:
    emitting X-rays toward an object while rotating an X-ray emitter around the object on a rotating frame of the CT apparatus;
    detecting, by second detector elements of a detector, the X-rays emitted from a plurality of points along a rotation path of the X-ray emitter, and generating projection data from the detected X-rays;
    obtaining scout images of the object;
    setting an imaging region of the object in the obtained scout images;
    determining an outline of the imaging region based on transverse axes lengths of the imaging region;
    controlling X-rays emitted toward the object by adjusting a distance between elements of a transverse collimator of the CT apparatus according to the determined outline; and
    reconstructing a cross-sectional X-ray image of the object based on X-ray projection data generated by detecting the controlled X-rays,
    wherein the scout images of the object comprise information about the transverse axes lengths of the imaging region at an angle at which the rotating frame rotates.

2. The method of claim 1, wherein the obtaining the scout images of the object comprises:
    acquiring obtaining the scout images by generating projection images of the object based on the projection data.

3. The method of claim 1, wherein the obtaining the scout images of the object comprises:
    acquiring obtaining the scout images by reconstructing cross-sectional X-ray images of the object from the projection data.

4. The method of claim 1, further comprising:
    displaying the scout images, the transverse axes lengths of the imaging region set in the scout images, and the determined outline.

5. The method of claim 4, further comprising changing the displayed outline based on a user input,
    wherein the controlling the X-rays comprises adjusting the distance between the elements of the transverse collimator according to an outline obtained by changing the displayed outline.

6. The method of claim 1, wherein the reconstructing the cross-sectional X-ray image of the object comprises:
    determining first detector elements which are to receive the controlled X-rays corresponding to the determined outline, of the detector;
    determining the second detector elements that actually detect the controlled X-rays;
    comparing the first detector elements with the second detector elements; and
    changing a position of a focal point of the X-rays emitted toward the object based on a comparison result.

7. The method of claim 1, wherein the CT apparatus comprises a detector comprising first detector elements which detect the controlled X-rays and third detector elements which are different from the first detector elements and do not detect the controlled X-rays,
    each of the first detector elements and of the third detector elements includes a memory, and
    wherein the reconstructing the cross-sectional X-ray image comprises storing the X-ray projection data generated from the controlled X-rays in the memories of the first detector elements and the memories of the second detector elements.

8. The method of claim 1, further comprising:
    representing the reconstructed cross-sectional X-ray image of the object in a region having a size which is greater than a size of the reconstructed cross-sectional X-ray image; and
    displaying a portion of the region, other than a portion on which the cross-sectional X-ray image is represented, in a predetermined color to thereby generate another cross-sectional X-ray image of the object having a greater size than that of the reconstructed cross-sectional X-ray image.

9. The method of claim 1, wherein the determining the outline comprises determining a longitudinal axis length of the imaging region set in one of the scout images, and
    the controlling of the X-rays comprises controlling the X-rays emitted toward the object by adjusting distances between the elements of the transverse collimator and between elements of a longitudinal collimator of the CT apparatus according to the outline and the longitudinal axis length, respectively.

10. The method of claim 1, wherein the controlling the X-rays further comprises determining the distance between the elements of the transverse collimator corresponding to the determined outline.

11. The method of claim 1, wherein the determining the outline comprises:

determining, from the scout images, the outline as an ellipse having major axes equal to the transverse axes lengths of the imaging region.

12. A non-transitory computer-readable recording medium having recorded thereon a program which, when executed by a computer, causes the computer to execute the method of claim 1.

13. A computed tomography (CT) apparatus comprising:

a rotating frame including:
an X-ray emitter configured to emit X-rays from a plurality of points along a rotation path of the rotating frame toward an object;
a transverse collimator configured to adjust a transverse axis length of the X-rays;
a detector configured to detect the X-rays at the plurality of points and generate projection data from the detected X-rays; and
a processor configured to obtain scout images of the object, set an imaging region of the object in the obtained scout images, determine an outline of the imaging region based on transverse axes lengths of the imaging region, control the X-rays emitted toward the object by adjusting a distance between elements of the transverse collimator according to the determined outline, and reconstruct a cross-sectional X-ray image of the object based on X-ray projection data generated by detecting the controlled X-rays,
wherein the scout images of the object comprise information about the transverse axes lengths of the imaging region at an angle at which the rotating frame rotates.

14. The CT apparatus of claim 13, wherein the processor is further configured to generate projection images of the object based on the projection data, and obtain the projection images of the object as the scout images.

15. The CT apparatus of claim 13, wherein the processor is further configured to reconstruct cross-sectional images of the object based on the projection data, and obtain the cross-sectional images of the object as the scout images.

16. The CT apparatus of claim 13, further comprising a display configured to display the scout images, the transverse axes lengths of the imaging region set in the scout images, and the determined outline.

17. The CT apparatus of claim 16, wherein the processor is further configured to change the displayed outline based on a user input, and control the X-rays emitted toward the object by adjusting the distance between the elements of the transverse collimator according to the changed outline.

18. The CT apparatus of claim 13, wherein the controller is further configured to determine first detector elements, of the detector, which are to receive the controlled X-rays corresponding to the determined outline, and second detector elements that actually detect the controlled X-rays, compare the first detector elements with the second detector elements, and change a position of a focal point of the X-rays emitted toward the object based on a comparison result.

19. The CT apparatus of claim 13, wherein the detector comprises first detector elements which detect the controlled X-rays and third detector elements which are different from the first detector elements and do not detect the controlled X-rays, each of the first detector elements and of the third detector elements includes a memory, and
the memories of the first detector elements and the memories of the third detector elements are configured to store the X-ray projection data generated from the controlled X-rays.

20. The CT apparatus of claim 13, wherein the processor is further configured to represent the reconstructed cross-sectional X-ray image of the object in a region having a size greater than a size of the reconstructed cross-sectional X-ray image, and display a portion of the region, other than a portion on which the cross-sectional X-ray image is represented, in a predetermined color to thereby generate another cross-sectional X-ray image of the object having a greater size than that of the reconstructed cross-sectional X-ray image.

21. The CT apparatus of claim 13, further comprising a longitudinal collimator configured to adjust a width of the X-rays in a longitudinal direction, wherein the processor is further configured to determine a longitudinal axis length of the imaging region set in one of the scout images, and
control the X-rays emitted toward the object by adjusting distances between the elements of the transverse collimator and between elements of the longitudinal collimator, of the X-ray emitter, according to the outline and the longitudinal axis length, respectively.

22. The CT apparatus of claim 13, wherein the processor is further configured to determine the distance between the elements of the transverse collimator corresponding to the determined outline.

* * * * *